United States Patent [19]

Antfang et al.

[11] Patent Number: 5,047,243

[45] Date of Patent: Sep. 10, 1991

[54] CARRIER GRANULES CONTAINING LIQUID ACTIVE COMPOUNDS

[75] Inventors: Elmar Antfang, Monheim; Dimitrios Kerimis, Cologne; Rolf-Jürgen Singer, Wuppertal, all of Fed. Rep. of Germany

[73] Assignee: Bayer Aktiengesellschaft, Leverkusen, Fed. Rep. of Germany

[21] Appl. No.: 461,208

[22] Filed: Jan. 5, 1990

[30] Foreign Application Priority Data

Jan. 18, 1989 [DE] Fed. Rep. of Germany ....... 3901273

[51] Int. Cl.$^5$ .............................................. A01N 25/34
[52] U.S. Cl. ..................................... 424/408; 424/405; 424/407; 424/409; 424/489; 514/919
[58] Field of Search ............... 424/405, 409, 410, 408, 424/407

[56] References Cited

U.S. PATENT DOCUMENTS

| | | | |
|---|---|---|---|
| 4,343,790 | 8/1982 | Pasarela | 514/127 |
| 4,485,103 | 11/1984 | Pasarela | 514/144 |
| 4,894,230 | 1/1990 | Friemel et al. | 424/405 |

FOREIGN PATENT DOCUMENTS

| | | | |
|---|---|---|---|
| 0162953 | 5/1953 | Australia | 424/406 |
| 2939746 | 8/1980 | Fed. Rep. of Germany | 424/406 |
| 2018593 | 10/1979 | United Kingdom | 424/408 |

Primary Examiner—Thurman K. Page
Assistant Examiner—James M. Spear
Attorney, Agent, or Firm—Sprung Horn Kramer & Woods

[57] ABSTRACT

In the combating of agricultural and horticultural pests by applying to a locus from which it is desired to exclude such pests a normally liquid active compound and a normally solid active compound, the improvement which comprises applying such active compound in the form of granules comprising a) carrier granules having a non-absorptive surface,
b) at least one liquid active compound,
c) at least one adhesive based on polyurethane as a binder, optionally mixed with a further adhesive selected from the group consisting of polyvinyl acetate, polyvinylpyrrolidine, polyvinyl alcohol, copolymers of vinyl acetate/di-n-butyl maleate, acrylic acid ester, vinyl acetate/ethylene, vinyl acetate/ethylene/vinyl chloride, vinyl acetate/acrylic acid ester, vinyl acetate/vinyl ester and styrene/acrylic acid ester, and
d) optionally an additive.

10 Claims, No Drawings

CARRIER GRANULES CONTAINING LIQUID ACTIVE COMPOUNDS

The present invention relates to new carrier granules containing liquid active compounds (so-called "monocarrier granules"). According to the invention, active compound is preferably understood as meaning the active components of the plant protection area, such as insecticides, nematicides, acaricides, fungicides, herbicides and growth regulators.

The invention furthermore relates to a process for the preparation of the new monocarrier granules and their use for combating pests, preferably in the agricultural and horticultural field.

Numerous carrier granules are already known which contain solid or liquid biocidal active compounds on a granular carrier material (compare Bühel, "Pflanzenschutz und Schädlingsbekämpfung" (Plant Protection and Pest Control), Georg-Thieme Verlag, Stuttgart, 1977, pages 198 and 199).

Carrier granules containing solid active compounds can thus be prepared, for example, by immobilizing the active components in finely divided form, if appropriate mixed with additives, on the compact or nonabsorptive surface of the carrier material with the aid of various adhesives. Carrier granules containing only liquid active compounds were unable to be prepared with sufficient resistance to abrasion by this method.

Carrier granules which contain liquid biocidal active compounds can be prepared, for example, by immersing porous or absorptive carrier materials in suitable solvents containing liquid active compounds or containing solutions of liquid active compounds, in each case optionally mixed with additives. The properties of these granules, however, are not always satisfactory. Because of the low hardness of the absorptive granules, these can abrade under the stress of physical forces and thus release biocide-containing dust.

New carrier granules containing liquid active compounds have now been found which contain
a) granular carrier material having a non-absorptive surface,
b) at least one liquid active compound,
c) at least one adhesive based on polyurethane as a binder, optionally mixed with a further adhesive based on one of the following systems: polyvinyl acetate, polyvinylpyrrolidone, polyvinyl alcohol, copolymers of vinyl acetate/di-n-butyl maleate, acrylic acid esters, vinyl acetate/ethylene, vinyl acetate/ethylene/vinyl chloride, vinyl acetate/acrylic acid esters, vinyl acetate/vinyl esters, styrene/acrylic acid esters and
d) optionally additives.

Furthermore, it has been found that the monocarrier granules according to the invention can be prepared by a process in which
granular carrier material having a non-absorptive surface is sprayed into a mixer with an aqueous dispersion of a polyurethane adhesive, optionally with the addition of a thickener and optionally mixed with an aqueous dispersion of a further adhesive based on one of the following systems: polyvinyl acetate, polyvinylpyrrolidone, polyvinyl alcohol, copolymers of vinyl acetate/di-n-butyl maleate, acrylic acid esters, vinyl acetate/ethylene, vinyl acetate/ethylene/vinyl chloride, vinyl acetate/acrylic acid esters, vinyl acetate/vinyl esters, styrene/acrylic acid esters, then a mixture containing the liquid active compounds and extenders is added, the product is optionally sprayed again with an aqueous dispersion of a further adhesive based on the abovementioned systems and the granular products thus obtained are dried.

Finally, it has been found that the monocarrier granules according to the invention can be used, depending on the active compounds contained, for a variety of purposes in agriculture and horticulture.

It is to be noted as extremely surprising that the monocarrier granules according to the invention show a better activity than previously known granules in which liquid active compounds are absorbed onto porous or absorptive carrier materials in the form of a solution. It is also advantageous that the polyurethane compounds used as adhesives are easily degraded under environmental conditions and release the active compound, protecting the active compound from chemical influences up to release.

The monocarrier granules according to the invention are distinguished by a number of advantages. The use of equipment adjusted to non-absorptive carrier material for the application of carrier granules for the monocarrier granules is thus possible without complicated readjustment.

In addition, the active compounds (active components) contained in these granules are released at their place of use in the manner desired in each case. Moreover, the monocarrier granules according to the invention are products which are distinguished by an extremely high resistance to abrasion.

The products according to the invention are described in the present case as monocarrier granules, the monocarrier granule containing at least one liquid biocidally active compound optionally in the form microencapsulation.

In the monocarrier granules according to the invention, all customary carrier substances contained in granules of this type and having a non-absorptive surface can be employed as granular carrier materials having a non-absorptive surface. Calcite, dolomite and sand, such as, for example, quartz sand, are preferable.

The average particle diameter of the carrier materials can be varied within a certain range. In general, the average particle diameter is between 0.1 and 3.0 mm, preferably between 0.3 and 1 mm.

Active compound components are understood as meaning in the present case, as already mentioned above, all active compounds which can customarily be used in plant protection. These preferably include insecticides, nematicides, acaricides, fungicides, herbicides and growth regulators.

The granules according to the invention contain at least one active compound liquid at room temperature for the monocarrier granule. Active compounds liquid at room temperature are preferably phosphoric acid derivatives. Examples which may be mentioned are:
O-ethyl O-(2-isopropyloxycarbonyl-phenyl) W-isopropylaminothionophosphate,
O,O-diethyl α-cyanobenzylidenamino-oxyphosphonothioate,
O,O-dimethyl O-(4-methylmercapto-3-methyl-phenyl)-thionophosphate,
O-ethyl O-(4-methylthio-phenyl) S-propyl-dithiophosphate, (O,O-diethyl-thionophosphoryl)-α-oximino-phenylacetonitrile, O,O-diethyl O-(3-chloro-4-methyl-7-coumarinyl)-thiophosphate, S-[1,2-bis-(ethoxycarbonyl)-ethyl] O,O-dimethyl dithiophosphate.

An adhesive based on polyurethane, optionally mixed with a further adhesive based on one of the following systems: polyvinyl acetate, polyvinylpyrrolidone, polyvinyl alcohol and with copolymers of vinyl acetate/di-n-butyl maleate, acrylic acid esters, vinyl acetate/ethylene, vinyl acetate/ethylene/vinyl chloride, vinyl acetate/acrylic acid esters, vinyl acetate/vinyl esters, styrene/acrylic acid esters functions as a binder in the monocarrier granules according to the invention.

Possible additives which may be present in the monocarrier granules according to the invention are extenders, dyes and also water and organic solvents.

In this connection, possible extenders are preferably fine-grain inorganic solids, such as ground natural minerals, for example kaolin, aluminas, talc, chalk, quartz powder, attapulgite, montmorillonite, sepiolite, zeolite, bentonite, and in addition ground synthetic minerals such as highly disperse silicic acids.

Inorganic pigments such as iron oxide, titanium dioxide, Prussian blue and organic dyes such as anthradinone, azo and metal phthalocyanine dyes may be mentioned as dyes which are suitable as additives.

Possible organic solvents are all organic solvents which can customarily be used for the preparation of carrier granules. Low-boiling organic solvents such as methanol, ethanol, butanol and methylene chloride are preferable.

The granules according to the invention consist of granular carrier materials, on the non-absorptive surface of which there is a covering layer which, for monocarrier granules, contains at least one liquid active compound. Polyurethane and mixtures of polyurethane and polyvinyl acetate, polyvinylpyrrolidone, polyvinyl alcohol, and mixtures with copolymers of vinyl acetate/di-n-butyl maleate, acrylic acid esters, vinyl acetate/ethylene, vinyl acetate/ethylene/vinyl chloride, vinyl acetate/acrylic acid esters, vinyl acetate/vinyl esters, and styrene/acrylic acid esters, which may optionally contain additives, act as binders. The components present in the covering layer may in some cases also penetrate into indentations in the carrier material.

The percentages of the components contained in the monocarrier granules according to the invention can be varied within a relatively large range. The proportion of granular carrier material is in general between 50 and 99.5% by weight, preferably between 60 and 92% by weight. The proportion of liquid active compounds is in general between 0.1 and 20% by weight, preferably between 0.5 and 15% by weight.

The proportion of the polyurethane and mixtures of polyurethane and polyvinyl acetate, polyvinylpyrrolidone, polyvinyl alcohol, and mixtures with copolymers of vinyl acetate/di-n-butyl maleate, acrylic acid esters, vinyl acetate/ethylene, vinyl acetate/ethylene/ vinyl chloride, vinyl acetate/acrylic acid esters, vinyl acetate/vinyl esters, and styrene/acrylic acid esters functioning as binding agents is in general between 0.1 and 4% by weight, preferably between 0.3 and 3% by weight, 0.05 to 0.49 part by weight, preferably 0.1 to 0.2 part by weight, of polyvinyl acetate, polyvinylpyrrolidone, polyvinyl alcohol and proportions of the copolymers mentioned above in general being apportioned per part of polyurethane. Additives are optionally present in proportions of 1 to 40 parts by weight, preferably 2 to 30 parts by weight.

In the preparation of the monocarrier granules according to the invention, preferably all those components are used which have already been mentioned as preferable in connection with the description of the monocarrier granules according to the invention.

The polyurethane functioning as a binder or the mixture of polyurethane and those components which have already been mentioned as preferable in connection with the description of the monocarrier granules according to the invention is, as already indicated above, employed as an aqueous dispersion. Suitable diluents in this connection in addition to water are also organic substances, preferably low-boiling organic solvents, such as methanol, ethanol, butanol and 1,2-dichloromethane.

When carrying out the process according to the invention, a process is in general employed in which granular carrier material having a non-absorptive surface is added to a mixer and, with continuous mixing, sprayed with an aqueous dispersion of polyurethane or a mixture of polyurethane and those components which have already been mentioned in connection with the description of the monocarrier granules according to the invention, at least one liquid active compound, optionally mixed with extenders, is then added, optionally sprayed again with an aqueous dispersion of polyurethane or a mixture of polyurethane and those components which have already been mentioned as preferable in connection with the description of the monocarrier granules according to the invention, and the granular products thus obtained are dried.

The sequence in which the components are applied to the carrier material can be varied in the manner desired in each case.

The process according to the invention is in general carried out at room temperature. However, it is also possible to work at somewhat elevated temperature.

The drying temperature can be varied within a relatively large range. In general, drying is carried out at granule temperatures between 20° C. and 70° C., preferably between 30° C. and 65° C. The drying can optionally be carried out under reduced pressure. In addition, the drying can either be carried out in the mixer used for coating the carrier material or else in a separate drying apparatus.

The process according to the invention can either be carried out batchwise or continuously in customary apparatus.

The monocarrier granules according to the invention can be employed, depending on the active components contained, for a large variety of purposes. Thus, they can be used, for example, for combating animal pests, fungi and/or weeds. If plant growth regulators are contained, they can also be employed for influencing the growth of cultivated plants.

Suitable adhesives based on polyurethane are those systems in which the actual polyurethane compound is formed by polyaddition of a partly esterified glycol, or symmetrical or unsymmetrical polyglycol with an excess of isocyanate, diisocyanate or polyisocyanate, free isocyanate groups being retained as prepolymers.

Polyurethanes are preferably employed which are prepared from a saturated polyester, formed from adipic acid and n-butanediol/n-hexanediol, by reaction with linear iso- or diisocyanates, free isocyanate groups being retained.

Chain-lengthening and formation of an aqueous dispersion takes place owing to reaction of the prepolymer formed in this way with mixtures of water and emulsifiers.

PREPARATION EXAMPLE 51.37 kg of grains of quartz sand having a diameter of 0.4 to 0.8 mm are sprayed with continuous mixing at room temperature (20° C.) into a mixer with 0.192 kg of an aqueous dispersion which contains 0.077 kg of polyurethane (prepared from adipic acid and n-butanediol/n-hexanediol and reaction with isocyanate, and further reaction of the prepolymers formed in this way with mixtures of water and emulsifiers).

1.155 kg of a finely ground pulverulent mixture, which contains 0.577 kg of the insecticidal compound of the formula

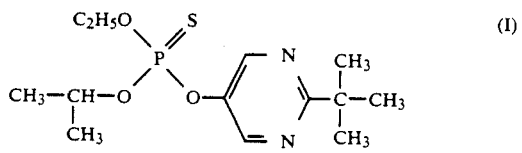

and 0.578 kg of highly disperse silicic acid, are then added at room temperature.

The grains of quartz sand coated with the pulverulent mixture are then sprayed with an aqueous dispersion which contains 0.22 kg of polyurethane adhesive of the above composition and a further 1.155 kg of the finely ground pulverulent mixture characterized above, which contains 0.577 kg of the active compound (I) and 0.385 kg of blue dye, are added with mixing.

The product is mixed for a further 10 minutes at room temperature and then dried in the mixer at a drying temperature of not more than 60° C.

55.0 kg of monocarrier granules having a content of 2.1% by weight of active compound of the formula (I) are obtained.

The granules are distinguished by a high resistance to abrasion.

COMPARISON EXAMPLE

Monocarrier granules based on polyvinyl acetate adhesive 93.4 g of grains of quartz sand having a diameter of 0.4 to 0.8 mm are sprayed with continuous mixing at room temperature into a mixer with an aqueous dispersion which contains 0.69 g of polyvinyl acetate. 2.10 g of a commercial finely ground pulverulent mixture, which contains 1.05 g of the compound of the formula (I)

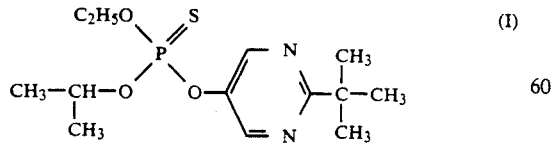

are then added at room temperature.

The grains of quartz sand coated with the pulverulent mixture are then sprayed with an aqueous dispersion which contains 0.69 g of polyvinyl acetate and 2.1 g of the finely ground pulverulent mixture, which contains 1.05 g of the active compound (I) and 0.7% of blue dye are added with mixing.

The product is mixed for a further 10 minutes at room temperature and then dried in the mixer at a drying temperature of not more than 60° C.

100 g of monocarrier granules having a content of 2.1% by weight of active compound of the formula (I) are thus obtained.

The granules thus obtained exhibited heavy abrasion and softening, so that they were not suitable for practical use.

It is understood that the specification and examples are illustrative but not limitative of the present invention and that other embodiments within the spirit and scope of the invention will suggest themselves to those skilled in the art.

We claim:

1. Carrier granules having an average particle diameter from 0.1 to 3 mm and containing liquid active compounds by weight comprising approximately
   a) 50 to 99.5% of carrier granules having a nonabsorptive surface,
   b) 0.1 to 20% of at least one liquid phosphoric acid derivative as active compound, and
   c) 0.1 to 4% of at least one adhesive based on polyurethane as a binder, optionally mixed with a further adhesive selected from the group consisting of polyvinyl acetate, polyvinylpyrrolidine, polyvinyl alcohol, copolymers of vinyl acetate/di-n-butyl maleate, acrylic acid ester, vinyl acetate/ethylene, vinyl acetate/ethylene/vinyl chloride, vinyl acetate/acrylic acid ester, vinyl acetate/vinyl ester and styrene/acrylic acid ester.

2. Carrier granules according to claim 1, wherein the active compound is a plant protection agent.

3. Carrier granules according to claim 1, wherein the active compound is a liquid phosphoric acid ester.

4. Carrier granules according to claim 1, containing as an additive at least one of an extender, dye, water and an organic solvent.

5. Carrier granules according to claim 1, containing fine-grain inorganic solids as an extender.

6. Carrier granules according to claim 1, containing an inorganic pigment as a dye.

7. Carrier granules according to claim 1, containing methanol, ethanol, butanol or methylene chloride as an organic solvent.

8. A process for the preparation of carrier granules containing liquid active compounds according to claim 1, comprising
   spraying into a mixer granular carrier material having a non-absorptive surface and an aqueous dispersion of a polyurethane adhesive, optionally with the addition of a thickener and optionally with an aqueous dispersion of a further adhesive selected from the group consisting of polyvinyl acetate, polyvinylpyrrolidone, polyvinyl alcohol, a copolymer of vinyl acetate/di-n-butyl maleate, acrylic acid ester, vinyl acetate/ethylene, vinyl acetate/ethylene/vinyl chloride, vinyl acetate/acrylic acid ester, vinyl acetate/vinyl ester and styrene/acrylic acid ester,
   then adding a mixture containing the liquid active compound and an extender, optionally again spraying the product with an aqueous dispersion of the further adhesive,
   and then drying the granules.

9. In the combating of agricultural and horticultural pests by applying to a locus from which it is desired to exclude such pests a normally liquid active compound and a normally solid active compound, the improvement which comprises applying such active compound in the form of granules according to claim 1.

10. Carrier granules according to claim 1 of an average particle diameter from 0.3 to 1 mm and by weight comprising approximately 60 to 92% of carrier granules, 0.5 to 15% of phosphoric acid derivative and 0.3 to 3% by weight of adhesive.

* * * * *